(12) United States Patent
Colone

(10) Patent No.: US 8,158,041 B2
(45) Date of Patent: Apr. 17, 2012

(54) RADIALLY EXPANDABLE POLYTETRAFLUOROETHYLENE

(75) Inventor: William M. Colone, Phoenix, AZ (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 345 days.

(21) Appl. No.: 11/966,444

(22) Filed: Dec. 28, 2007

(65) Prior Publication Data

US 2008/0143011 A1 Jun. 19, 2008

Related U.S. Application Data

(60) Division of application No. 10/772,703, filed on Feb. 5, 2004, now Pat. No. 7,465,483, which is a continuation of application No. 08/888,438, filed on Jul. 7, 1997, now abandoned, which is a continuation of application No. 08/701,543, filed on Aug. 22, 1996, now abandoned, which is a continuation of application No. 08/265,794, filed on Jun. 27, 1994, now abandoned.

(51) Int. Cl.
*B27J 5/00* (2006.01)

(52) U.S. Cl. ........... 264/127; 264/209.5; 264/211; 264/230; 428/36.5; 428/36.9; 623/1.49; 623/901

(58) Field of Classification Search ........... 264/119, 264/127, 209.5, 211, 230; 623/1.1, 1.43, 623/1.54, 1.49, 901; 521/919; 428/36.5, 428/36.9

See application file for complete search history.

(56) References Cited

U.S. PATENT DOCUMENTS

| | | | |
|---|---|---|---|
| 3,008,187 A | 11/1961 | Slade | |
| 3,260,774 A | 7/1966 | Harlow | |
| 3,389,201 A | 6/1968 | Alsup at al. | |
| 3,391,221 A | 7/1968 | Gore at al. | |
| 3,953,566 A | 4/1976 | Gore | |
| 3,962,153 A | 6/1976 | Gore | |
| 4,025,679 A | 5/1977 | Denny | |
| 4,104,394 A | 8/1978 | Okita et al. | |
| 4,110,392 A | 8/1978 | Yamazaki et al. | |
| 4,187,390 A | 2/1980 | Gore | |
| 4,208,745 A * | 6/1980 | Okita | 623/1.4 |
| 4,229,838 A | 10/1980 | Mano et al. | |
| 4,250,138 A | 2/1981 | Okita et al. | |
| 4,277,429 A | 7/1981 | Okita et al. | |
| 4,283,448 A | 8/1981 | Bowman | |
| 4,321,711 A * | 3/1982 | Mano | 623/1.43 |
| 4,332,035 A | 6/1982 | Mano et al. | |

(Continued)

FOREIGN PATENT DOCUMENTS

EP 0059619 A1 9/1982

(Continued)

OTHER PUBLICATIONS

Mar. 19, 2010 European Search Report for EP application No. 05075839.0 filed Jun. 7, 1995.

*Primary Examiner* — Richard Crispino
*Assistant Examiner* — Elizabeth Royston
(74) *Attorney, Agent, or Firm* — Rutan & Tucker, LLP

(57) ABSTRACT

Extruded, stretched, sintered tubular PTFE materials are produced which are suited for use in the medical field as liners and covers for expandable stents. The PTFE materials have an unusually low REC (Radial Expansion Coefficient) and RER (Radial Expansion Ratio).

20 Claims, 1 Drawing Sheet

U.S. PATENT DOCUMENTS

| | | | |
|---|---|---|---|
| 4,385,093 A | 5/1983 | Hubis | |
| 4,478,665 A | 10/1984 | Hubis | |
| 4,482,516 A | 11/1984 | Bowman et al. | |
| 4,496,507 A | 1/1985 | Okita et al. | |
| 4,560,374 A | 12/1985 | Hammerslag | |
| 4,576,869 A | 3/1986 | Malhotra | |
| 4,733,665 A | 3/1988 | Palmaz | |
| 4,743,251 A | 5/1988 | Barra et al. | |
| 4,776,337 A | 10/1988 | Palmaz | |
| 4,826,725 A | 5/1989 | Harlow | |
| 4,830,062 A | 5/1989 | Yamamoto et al. | |
| 4,876,051 A | 10/1989 | Campbell et al. | |
| 4,877,661 A | 10/1989 | House et al. | |
| 4,893,623 A * | 1/1990 | Rosenbluth | 606/192 |
| 4,922,905 A | 5/1990 | Strecker et al. | |
| 4,973,609 A | 11/1990 | Browne | |
| 5,026,513 A | 6/1991 | House et al. | |
| 5,071,609 A | 12/1991 | Tu et al. | |
| 5,078,726 A | 1/1992 | Kreamer | |
| 5,098,625 A | 3/1992 | Huang et al. | |
| 5,108,424 A | 4/1992 | Hoffman, Jr. et al. | |
| 5,110,527 A * | 5/1992 | Harada et al. | 264/127 |
| 5,122,154 A | 6/1992 | Rhodes | |
| 5,123,917 A | 6/1992 | Lee | |
| 5,217,483 A | 6/1993 | Tower | |
| 5,219,355 A | 6/1993 | Parodi et al. | |
| 5,258,020 A | 11/1993 | Froix | |
| 5,282,860 A | 2/1994 | Matsuno et al. | |
| 5,308,664 A | 5/1994 | House et al. | |
| 5,316,023 A | 5/1994 | Palmaz et al. | |
| 5,321,109 A | 6/1994 | Bosse et al. | |
| 5,360,443 A | 11/1994 | Barone et al. | |
| 5,383,928 A | 1/1995 | Scott et al. | |
| 5,389,106 A | 2/1995 | Tower | |
| 5,425,765 A | 6/1995 | Tiefenbrun et al. | |
| 5,468,138 A | 11/1995 | Bosse et al. | |
| 5,618,300 A | 4/1997 | Marin et al. | |
| 5,662,713 A | 9/1997 | Andersen et al. | |
| 5,876,445 A | 3/1999 | Andersen et al. | |
| 6,620,190 B1 | 9/2003 | Colone | |

FOREIGN PATENT DOCUMENTS

| | | |
|---|---|---|
| EP | 0269449 A2 | 6/1988 |
| WO | WO-9404097 A1 | 3/1994 |

* cited by examiner

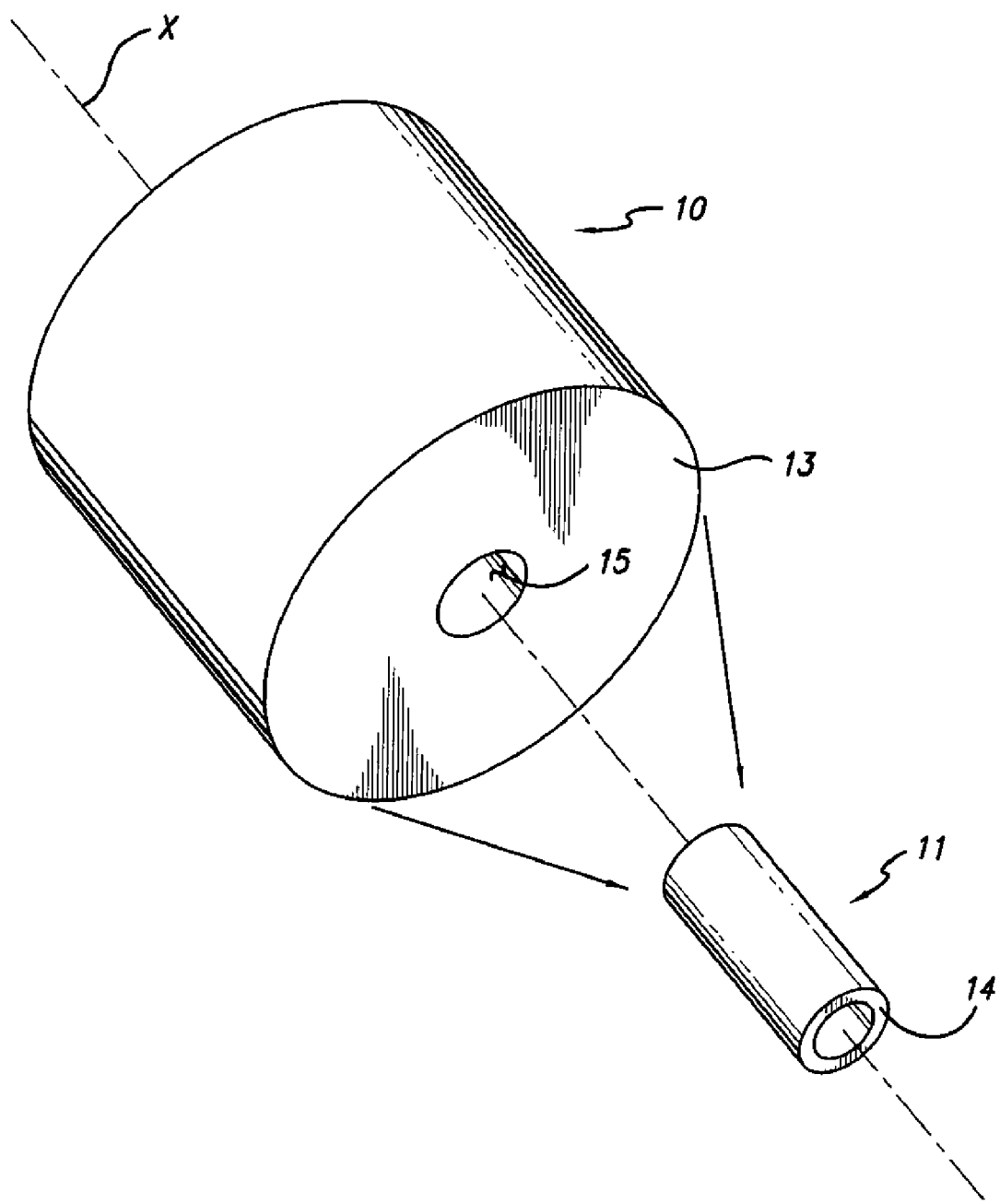

RADIALLY EXPANDABLE POLYTETRAFLUOROETHYLENE

PRIORITY

This application is a division of U.S. patent application Ser. No. 10/772,703, filed Feb. 5, 2004, now U.S. Pat. No. 7,465,483, which is a continuation of U.S. patent application Ser. No. 08/888,438, filed Jul. 7, 1997, now abandoned, which is a continuation of U.S. patent application Ser. No. 08/701,543, filed Aug. 22, 1996, now abandoned, which is a continuation of U.S. patent application Ser. No. 08/265,794, filed Jun. 27, 1994, now abandoned, each of which is incorporated by reference into this application as if fully set forth herein.

BACKGROUND

This invention relates to polytetrafluoroethylene (hereinafter PTFE) materials which, after being radially expanded, retain their structural integrity.

More particularly, the invention relates to extruded, stretched, sintered tubular PTFE materials suited for use in the medical field as liners and covers for expandable stents.

The use of expandable endovascular stents to open and support aortic blood vessels is well known in the art. Such stents, which are typically made from stainless steel, are thrombogenic and tend to occlude due to growth of tissue through the stent into the blood vessel. The length of such stents is also limited because of their rigidity. Consequently, liners and covers have been sought for use in conjunction with metallic stents in order to shield the stent and to extend the length of anatomy which can be treated with the stent. The development of acceptable stent liners or covers has been slow because the liners or covers preferably must (1) expand with the stent, (2) be non-thrombogenic, (3) be biocompatible, (4) be inert, (5) have a low profile with the ability to expand up to about four times its original dimension, (6) be expandable at low pressures of less than five to ten atmospheres to reduce the risk of injury to the patient, (7) retain its physical properties and structural strength after being expanded, (8) generally not alter its length after being expanded, (9) be impervious to blood at physiological pressures, (10) conform to host anatomy when expanded, (11) resist the growth of bodily tissue therethrough, (12) be able to carry radiopaque markings for location during fluoroscopy.

Paste-formed, extruded tubular PTFE products are well known, as are paste extrusion and paste forming manufacturing processes for producing such products. During such manufacturing processes, a PTFE resin is mixed with a liquid lubricant. A preformed resin—lubricant charge is then produced and extruded through an annular orifice to produce an unsintered PTFE tube. The extruded tube is heated to remove the lubricant and produce a porous, unsintered PTFE tube. The tube typically has a density of from 1.5 to about 1.75 gm/cc and accompanying porosities of 39% to 26%. If the unsintered tube sintered by heating the tube to a temperature above its crystalline melting temperature, a nonporous tube results. See U.S. Pat. Nos. 3,953,566, 3,962,153, 4,110,392, 4,187,390, 4,283,448, 4,385,093, 4,478,665, 4,482,516, 4,877,661, and 5,026,513.

In the medical field, PTFE products are used as replacement veins and arteries. PTFE is inert, is non-thrombogenic, and has other characteristics desirable for a stent cover or liner. Commercially available PTFE medical tubular products have, however, significant radial strength and are not readily dilated. Conventional PTFE tubes typically have a high radial strength and rapidly lose their tensile strength and become weak and thin after being dilated by only small amounts.

Accordingly, it would be highly desirable to provide improved PTFE products which can be readily expanded and which, after being expanded, substantially retain their tensile strength and other physical properties which make the use of PTFE in the body desirable.

BRIEF SUMMARY

Therefore, it is a principal object of the invention to provide improved PTFE products which are amenable to use as liners and covers for expandable stents.

A further object of the invention is to provide improved tubular PTFE products which substantially retain their structural integrity after the products are radially expanded.

Another object of the invention is to extend the length of anatomy which can be treated with an expandable stent.

I have discovered new PTFE products and a process and composition for producing the same. The new PTFE products can be significantly expanded to configurations which retain their structural integrity and which substantially retain their tensile strength and other desirable physical properties. As discussed in detail in the examples below, the new PTFE products have an unusually low REC (Radial Expansion Coefficient) and RER (Radial Expansion Ratio) which function to permit thin-walled PTFE tubes to expand about 50% to 400% before the tubes lose their structural integrity and suffer a rapid decline in tensile strength. The new PTFE products can also be pre-dilated to insure that an RER equal to one will be achieved.

Other features and advantages will become apparent from the following description and from the claims. The following examples are presented to illustrate the presently preferred embodiments of and practice of the invention and not by way of limitation of the scope of the invention.

BRIEF DESCRIPTION OF THE DRAWING

FIG. 1 is a diagrammatic view of a preform and an extruded tube.

DETAILED DESCRIPTION

Examples 1-17, below, concern expandable PTFE material formed as a result of stretching and subsequent sintering, as described in U.S. Pat. No. 6,620,190, which is incorporated by reference into this application as if fully set forth herein. Examples 18-23, below, concern expandable PTFE material formed as a result of expansion in a first dimension, sintering, pre-dilating to a second dimension, and re-sintering.

Example 1

One hundred grams of FLUON CD 123 resin produced by ICI Americas, Inc. was sifted through a No. 10 sieve and then blended at room temperature with twenty-five grams of ISOPAR M solvent produced by Exxon Corporation to produce a preform blend. Other lubricants well known in the art includes VM&P NAPHTHA (boiling point (bp) 118-130° C.), ISOPAR (Registered trademark of Exxon Corporation), ISOPAR 3 G (bp 159-174° C.), ISOPAR H (bp 176-189° C.), Low Odor Paraffin Solvent (bp 191-246° C.), and SHELLSOL (Trademark of Shell Oil) K.

The resulting preform blend was allowed to sit for over eight hours before being re-sifted through a No. 10 sieve. The lubricant level (LL) equals the weight of solvent used divided by the weight of resin used, which means the lubricant level utilized in this Example 1 was 25%. In the practice of the invention the lubricant level is normally in the range of 16% to 35%, and is presently preferably in the range of about 18% to 25%.

Referring now to FIG. 1, a preform charge 10 was created by compacting the preform blend under 200 to 400 psi for approximately one minute in a stainless steel cylinder containing a center shaft. The center shaft extended along the centerline X of the cylinder and was concentric with the cylinder. The resulting preform charge 10 was a hollow cylindrical mass having a doughnut shaped circular cross sectional area 13, as shown in FIG. 1. The cylindrical hollow midsection 15 in the preform charge 10 was occupied by the center shaft. The preform charge 10 was then loaded into a cylindrical barrel in a ram extruder and was extruded into several individual lengths of cylindrical thin-walled tubing 11 at a reduction ratio (RR) of 125:1. The total length of tubing 11 produced from the preform charge 10 was about twenty feet. The extruded tubing 11 had a microstructure characterized by nodes interconnected by fibrils. The reduction ratio equals the ratio of the cross sectional area 13 of the preform charge 10 to the cross sectional area 14 of the wall of the tubing 11. In the practice of the invention, the RR is less than 200 or 300 to 1; preferably equal to or less than 125:1. The ratio of the RR to the LL in the practice of the invention is preferably less than five. In prior art preform blends, the ratio of the RR to the LL is normally greater than five, and is typically nine or greater.

The solvent was removed from the extruded tubing by placing the tubes in a forced-air circulation electric oven at 255 degrees C. for thirty minutes. As used herein, the length of the tube after it is extruded and heated at 255 degrees C. to remove the solvent is termed the original length of the tube.

After being heated to 255 degrees C., each tube was heated to 290 degrees C. for five minutes and then stretched longitudinally at rate of about 100% per second to a length four times the original length of the tube. Each tube can, if desired, be stretched at a rate in the range of 5% to 500% per second and stretched to a length in the range of two to six times the original length of the tube.

The stretched porous tubes were then sintered at approximately 360 degrees C. for forty-five to 90 seconds. The sintering crystallized the PTFE and increased the strength of the porous tubes. During sintering each end of the tubes was restrained to prevent longitudinal shrinkage of the tube. The resulting stretched, sintered, porous tubes consisted essentially of highly crystalline PTFE polymer and had a microstructure characterized by nodes interconnected by fibrils.

The FLUON CD 123 resin is a white, free-flowing powder made by coagulation of an aqueous dispersion of polytetrafluoroethylene (PTFE). It is designed for paste extrusion with volatile hydrocarbon lubricants for applications in which opacity in the sintered article is not a problem. FLUON CD123 has a relatively high molecular weight. Unsintered extrudates exhibit good green strength.

| TYPICAL PROPERTIES OF FLUON CD 123 | | | |
|---|---|---|---|
| Property | Nominal Value | Units | Test Method |
| Apparent Density | 500 | grams/liter | ASTM D 1457-83 |
| Median Particle Size | 500 | microns | ASTM D 1457-83 |
| Melting Point | 327 | ° C. | ASTM D 1457-83 |
| Color | White | | |
| Specific Gravity | 2.16-2.18 | | ASTM D 1457-83 |

| TYPICAL PROPERTIES OF FLUON CD 123 (continued) | | | |
|---|---|---|---|
| Property | Nominal Value | Units | Test Method |
| Moisture Content (Max.) | 0.04 | % | ASTM D 1457-83 |
| Extrusion Pressure | 15000 | psi | |

Example 2

Example 1 was repeated except that twenty grams of ISOPAR M solvent was utilized instead of twenty-five grams and the pre-form charge was extruded at a reduction ratio (RR) of 91:1 into cylindrical thin-walled tubing. Approximately twenty feet of cylindrical tubing was produced.

Example 3

Example 1 was repeated except that eighteen grams of ISOPAR M solvent was utilized instead of twenty-five grams and the pre-form charge was extruded at a reduction ratio (RR) of 48:1 into cylindrical thin-walled tubing. Approximately ten feet of thin-walled tubing was produced.

Example 4

Example 1 was repeated except that eighteen grams of ISOPAR M solvent was utilized instead of twenty-five grams; ninety-five grams of CD123 was utilized instead of one hundred grams; five grams of CD509 was combined with the ISOPAR M solvent and the CD123; and, the resulting preform charges was extruded at a reduction ratio (RR) of 48:1 into cylindrical thin-walled tubing. Approximately ten feet of thin-walled tubing was produced.

The FLUON CD509 resin is a white, free-flowing powder made by coagulation of an aqueous dispersion of polytetrafluoroethylene (PTFE). It is designed for paste extrusion at medium to high reduction ratios where high sintering rates are desirable.

| TYPICAL PROPERTIES OF FLUON CD 509 | | | |
|---|---|---|---|
| Property | Nominal Value | Units | Test Method |
| Apparent Density | 500 | grams/liter | ASTM D 1457-83 |
| Median Particle Size | 500 | microns | ASTM D 1457-83 |
| Melting Point | 327 | ° C. | ASTM D 1457-83 |
| Color | White | | |
| Specific Gravity | 2.18-2.20 | | ASTM D 1457-83 |
| Moisture Content (Max.) | 0.04 | % | ASTM D 1457-83 |
| Extrusion Pressure | 8700 | psi | |

Example 5

Three tubes approximately thirty-five centimeters long produced in Example 1 were each tested as follows.

An appropriate size angioplasty balloon catheter manufactured by Boston Scientific was placed in the inner lumen of the tube and was inflated with water with a standard MONARCH endoflater at a rate of approximately ten psi per second. Merit Medical manufactures the MONARCH endoflater. The balloon was about four centimeters long. As is well known, the balloon catheter is normally inserted in a blood vessel by first inserting a wire in a vessel; then inserting a vessel dilator along the wire into the vessel; removing the vessel dilator; inserting an introducer sleeve along the wire into the vessel; inserting the balloon; removing the introducer sleeve; inflating the balloon; deflating the balloon; removing the balloon; and removing the wire. A similar procedure was used while utilizing the balloon catheter to test the PTFE tubes of Example 1.

The balloon catheter did not apply an outward expansion force against the tube until the catheter was inflated under pressure with water. Inflation of the balloon (and the concomitant increase in inflation pressure) was stopped at predetermined pressure intervals of one or one-half atmosphere pressure to measure the outside diameter of each tube. Each tube was dilated until it burst.

The actual inflation pressure was observed on a digital pressure gauge and recorded. The percent dilatation was calculated by measuring the tubing outside diameter with digital calipers at each pressure interval and then using the following formula:

% Dilatation=$[(D_d-D_i)/(D_i)] \times 100$ where $D_i$=initial tube diameter at pressure equal to zero
$D_d$=measured dilated tubing diameter From the raw data, REC (Radial Expansion Coefficient), REL (Radial Expansion Limit), and RER (Radial Expansion Ratio) were calculated and recorded along with the calculated reduction ratio to lubricant level ratio (RR/LL), where:

$P_{max}$=Maximum Inflation Pressure
$P_{burst}$=Burst Inflation Pressure
% RD=Percent Radial Dilatation
REC=$(P_{max})/$(% RD at $P_{max}$)
REL=$(P_{burst})/$(% RD at $P_{burst}$)
RER=(REC)/(REL)

As used herein, a tube retains its structural integrity after being radially expanded as long as the tube requires the application of an increased inflation pressure before the amount of radial expansion of the tube increases. If a tube continues to expand when the amount of inflation pressure decreases, then the tube has lost its structural integrity. When the $P_{max}$ of a tube is exceeded, the tube loses its structural integrity. However, the loss in structural integrity results in degradations of physical properties which are significantly less than those which occur in prior art PTFE tubes. For example, at a percent dilatation of about 300% in Table I below, the tube still retains about 70% to 75% of its pre-dilatation tensile strength. Also, in Table I below, Tube No. 1 loses its structural integrity at an inflation pressure greater than 6.5 atm ($P_{max}$). In Tables II and III below, Tubes No. 2 and 3, respectively also lose their structural integrity at an inflation pressure greater than 6.5 atm ($P_{max}$).

The following results were obtained for the three Example 1 tubes which were tested:

Tube No. 1

TABLE I

| | Tube No. 1 Measurements | | |
|---|---|---|---|
| Measurement | Inflation Pressure (Atm) | Diameter (mm) | % Dilatation |
| 1 | 0 | 2.75 | — |
| 2 | 1 | 2.75 | 0 |
| 3 | 2 | 2.75 | 0 |
| 4 | 3 | 3.05 | 11 |
| 5 | 3.5 | 3.13 | 14 |
| 6 | 4 | 3.20 | 16 |
| 7 | 4.5 | 3.34 | 21 |
| 8 | 5 | 3.37 | 23 |
| 9 | 5.5 | 3.92 | 43 |

TABLE I-continued

| | Tube No. 1 Measurements | | |
|---|---|---|---|
| Measurement | Inflation Pressure (Atm) | Diameter (mm) | % Dilatation |
| 10 | 6 | 4.62 | 68 |
| 11 | 6.5 ($P_{max}$) | 5.34 | 94 |
| 12 | 4.5 ($P_{burst}$) | 12.12 | 341 |

REC = (6.5 atm × 14.7 psi/atm)/94% = 1.02 psi/%
REL = (4.5 atm × 14.7 psi/atm)/341% = 0.19 psi/%
RER = (1.02)/(0.19) = 5.4

Tube No. 2

TABLE II

| | Tube No. 2 Measurements | | |
|---|---|---|---|
| Measurement | Inflation Pressure (Atm) | Diameter (mm) | % Dilatation |
| 1 | 0 | 2.67 | — |
| 2 | 1 | 2.67 | 0 |
| 3 | 2 | 2.87 | 7 |
| 4 | 3 | 3.02 | 13 |
| 5 | 3.5 | 3.02 | 13 |
| 6 | 4 | 3.17 | 19 |
| 7 | 4.5 | 3.23 | 21 |
| 8 | 5 | 3.40 | 27 |
| 9 | 5.5 | 3.64 | 36 |
| 10 | 6 | 4.77 | 79 |
| 11 | 6.5 ($P_{max}$) | 5.51 | 106 |
| 12 | 4.5 ($P_{burst}$) | 12.51 | 369 |

REC = (6.5 atm × 14.7 psi/atm)/106% = 0.90 psi/%
REL = (4.5 atm × 14.7 psi/atm)/369% = 0.18 psi/%
RER = (0.90)/(0.18) = 5.0

Tube No. 3

TABLE III

| | Tube No. 3 Measurements | | |
|---|---|---|---|
| Measurement | Inflation Pressure (Atm) | Diameter (mm) | % Dilatation |
| 1 | 0 | 2.75 | — |
| 2 | 1 | 2.75 | 0 |
| 3 | 2 | 2.75 | 0 |
| 4 | 3 | 3.05 | 11 |
| 5 | 3.5 | 3.13 | 14 |
| 6 | 4 | 3.20 | 16 |
| 7 | 4.5 | 3.34 | 21 |
| 8 | 5 | 3.37 | 23 |
| 9 | 5.5 | 3.92 | 43 |
| 10 | 6 | 4.62 | 68 |
| 11 | 6.5 ($P_{max}$) | 5.34 | 94 |
| 12 | 4.5 ($P_{burst}$) | 12.97 | 372 |

REC = (6.5 atm × 14.7 psi/atm)/94% = 0.90 psi/%
REL = (4.5 atm × 14.7 psi/atm)/371% = 0.18 psi/%
RER = (0.90)/(0.18) = 5.7

Example 6

Three tubes approximately thirty-five centimeters long produced in Example 2 were each tested utilizing the equipment and procedure described in EXAMPLE 5. The following results were obtained for the three Example 2 tubes tested.

Tube No. 1

TABLE IV

Tube No. 1 Measurements

| Measurement | Inflation Pressure (Atm) | Diameter (mm) | % Dilatation |
|---|---|---|---|
| 1 | 0 | 4.27 | — |
| 2 | 1 | 4.27 | 0 |
| 3 | 2 | 4.27 | 0 |
| 4 | 3 | 4.35 | 2 |
| 5 | 3.5 | 5.85 | 37 |
| 6 | 4 ($P_{max}$) | 9.08 | 113 |
| 7 | 2.5 ($P_{burst}$) | 16.39 | 284 |

REC = (4.0 atm × 14.7 psi/atm)/113% = 0.52 psi/%
REL = (2.5 atm × 14.7 psi/atm)/284% = 0.13 psi/%
RER = (0.52)/(0.13) = 4.0

Tube No. 2

TABLE V

Tube No. 2 Measurements

| Measurement | Inflation Pressure (Atm) | Diameter (mm) | % Dilatation |
|---|---|---|---|
| 1 | 0 | 4.74 | — |
| 2 | 1 | 4.74 | 0 |
| 3 | 2 | 4.74 | 0 |
| 4 | 3 | 5.49 | 16 |
| 5 | 3.5 | 7.09 | 50 |
| 6 | 4 ($P_{max}$) | 10.00 | 111 |
| 7 | 3 ($P_{burst}$) | 20.52 | 333 |

REC = (4 atm × 14.7 psi/atm)/111% = 0.53 psi/%
REL = (3 atm × 14.7 psi/atm)/333% = 0.13 psi/%
RER = (0.53)/(0.13) = 4.1

Tube No. 3

TABLE VI

Tube No. 3 Measurements

| Measurement | Inflation Pressure (Atm) | Diameter (mm) | % Dilatation |
|---|---|---|---|
| 1 | 0 | 4.83 | — |
| 2 | 1 | 4.83 | 0 |
| 3 | 2 | 4.83 | 0 |
| 4 | 3 | 5.23 | 8 |
| 5 | 3.5 | 6.00 | 24 |
| 6 | 4 ($P_{max}$) | 9.66 | 100 |
| 7 | 3 ($P_{burst}$) | 18.12 | 275 |

REC = (4 atm × 14.7 psi/atm)/100% = 0.59 psi/%
REL = (3 atm × 14.7 psi/atm)/275% = 0.16 psi/%
RER = (0.59)/(0.16) = 3.7

Example 7

Two tubes approximately thirty-five centimeters long produced in Example 3 were each tested utilizing the equipment and procedure described in EXAMPLE 5. The following results were obtained for the two tubes tested.

Tube No. 1

TABLE VII

Tube No. 1 Measurements

| Measurement | Inflation Pressure (Atm) | Diameter (mm) | % Dilatation |
|---|---|---|---|
| 1 | 0 | 6.04 | — |
| 2 | 1 | 6.28 | 4 |
| 3 | 1.5 | 6.45 | 7 |
| 4 | 2 | 6.79 | 12 |
| 5 | 2.5 | 7.15 | 18 |
| 6 | 3 | 7.39 | 22 |
| 7 | 3.5 | 8.33 | 38 |
| 8 | 4 ($P_{max}$) | 9.82 | 63 |
| 9 | 3.7 ($P_{burst}$) | 24.77 | 310 |

REC = (4.0 atm × 14.7 psi/atm)/63% = 0.93 psi/%
REL = (3.7 atm × 14.7 psi/atm)/310% = 0.18 psi/%
RER = (0.93)/(0.18) = 5.2

Tube No. 2

TABLE VIII

Tube No. 2 Measurements

| Measurement | Inflation Pressure (Atm) | Diameter (mm) | % Dilatation |
|---|---|---|---|
| 1 | 0 | 5.99 | — |
| 2 | 1 | 6.65 | 11 |
| 3 | 1.5 | 6.76 | 13 |
| 4 | 2 | 7.01 | 17 |
| 5 | 2.5 | 7.31 | 22 |
| 6 | 3 | 7.73 | 29 |
| 7 | 3.5 | 8.43 | 41 |
| 8 | 4 | 9.09 | 52 |
| 9 | 4.5 ($P_{max}$) | 11.17 | 86 |
| 10 | 3.9 ($P_{burst}$) | 25.62 | 328 |

REC = (4.5 atm × 14.7 psi/atm)/86% = 0.77 psi/%
REL = (3.9 atm × 14.7 psi/atm)/328% = 0.17 psi/%
RER = (0.77)/(0.17) = 4.5

Example 8

Two tubes approximately thirty-five centimeters long produced in Example 4 were each tested utilizing the equipment and procedure described in EXAMPLE 5. The following results were obtained for the two tubes tested.

Tube No. 1

TABLE IX

Tube No. 1 Measurements

| Measurement | Inflation Pressure (Atm) | Diameter (mm) | % Dilatation |
|---|---|---|---|
| 1 | 0 | 5.94 | — |
| 2 | 1 | 6.40 | 8 |
| 3 | 1.5 | 6.55 | 10 |
| 4 | 2 | 7.02 | 18 |
| 5 | 2.5 | 7.58 | 28 |
| 6 | 3 | 9.51 | 60 |
| 7 | 3.5 ($P_{max}$) | 13.15 | 121 |
| 8 | 2.9 ($P_{burst}$) | 24.15 | 307 |

REC = (3.5 atm × 14.7 psi/atm)/121% = 0.43 psi/%
REL = (3.9 atm × 14.7 psi/atm)/328% = 0.14 psi/%
RER = (0.43)/(0.14) = 3.1

Tube No. 2

TABLE X

Tube No. 2 Measurements

| Measurement | Inflation Pressure (Atm) | Diameter (mm) | % Dilatation |
|---|---|---|---|
| 1 | 0 | 5.90 | — |
| 2 | 1 | 6.41 | 9 |
| 3 | 1.5 | 6.89 | 17 |
| 4 | 2 | 7.09 | 20 |
| 5 | 2.5 | 7.83 | 33 |
| 6 | 3 | 8.34 | 41 |
| 7 | 3.5 | 9.90 | 68 |
| 8 | 4 ($P_{max}$) | 13.05 | 121 |
| 9 | 3.1 ($P_{burst}$) | 24.76 | 320 |

REC = (4 atm × 14.7 psi/atm)/121% = 0.49 psi/%
REL = (3.1 atm × 14.7 psi/atm)/320% = 0.14 psi/%
RER = (0.49)/(0.14) = 3.5

Example 9

Example 5 is repeated, except that after measurements are made at each pressure interval which causes the tube to dilate, the pressure is reduced by about one atmosphere to give the tube an opportunity to contract and five minutes later the diameter of the tube is remeasured. For example, after measurement no. 4 in Table I, the pressure is reduced to two atmospheres and five minutes later the diameter of the tube is remeasured; after example 5 in Table I, the pressure is reduced to two and a half atmospheres and five minutes later the diameter of the tube is remeasured; etc. Each time the diameter of the tube is remeasured, the diameter of the tube is reduced by about 10% or less from the measurement made when the pressure was one atmosphere greater. For example, after measurement no. 4 (3.05 mm) is taken in Table I, the water pressure is reduced to two atmospheres, and the diameter of the tube is measured five minutes later, the diameter of the tube is 2.75 mm.

Example 10

Example 1 is repeated except that the stretch rate is 10% per second instead of 100% per second.

Example 11

Example 1 is repeated except that the stretch rate is 300% per second instead of 100% per second.

Example 12

Example 1 is repeated except that the tube is stretched to three times its original length instead of four times its original length.

Example 13

Example 1 is repeated except that the tube is stretched to six times its original length instead of four times its original length.

Example 14

Example 5 is repeated utilizing tubes produced during Example 10. Similar results are obtained.

Example 15

Example 5 is repeated utilizing tubes produced during Example 11. Similar results are obtained.

Example 16

Example 5 is repeated utilizing tubes produced during Example 12. Similar results are obtained.

Example 17

Example 5 is repeated utilizing tubes produced during Example 13. Similar results are obtained.

As described in the above examples, a porous hollow tube (or sheet or other shape) which consists essentially of highly crystalline polytetrafluoroethylene polymer and which has a microstructure characterized by nodes interconnected by fibrils is formed by extruding a lubricant—polytetrafluoroethylene resin composition into a hollow tube, by heating the tube to remove the lubricant, by stretching the tube, and, while holding the tube in its stretched configuration, by sintering the tube at or above the melting temperature of the polytetrafluoroethylene resin to form a porous highly crystalline polytetrafluoroethylene polymer tube. This sintered porous tube of highly crystalline PTFE polymer has original inner and outer diameters.

As used herein, the terminology "radially pre-dilated" means that a porous highly crystalline polytetrafluoroethylene polymer tube is first radially dilated to increase the original inner (and outer) diameter of the tube and is then sintered to cause the dilated tube to contract radially to a configuration in which the diameter of the tube is less than the radially dilated diameter. When the radially dilated tube is sintered, the dilated tube is presently preferably contracted to a configuration in which the diameter of the tube substantially equals its original inner diameter. For example, and not by way of limitation, a sintered porous (the word "porous" indicates the extruded tube has been stretched along its longitudinal axis subsequent to being heated to remove lubricant and prior to being sintered to form highly crystalline PTFE polymer) tube of highly crystalline PTFE polymer having an inner diameter of six mm is radially pre-dilated by radially dilating the tube to an inner diameter (ID) of fifteen millimeters and by then sintering the tube to cause the tube to radially contract to an inner diameter of six mm. Similarly, the three mm ID sintered porous tube of highly crystalline PTFE polymer is radially pre-dilated by radially dilating the tube to an ID of six millimeters and by then sintering the tube to cause the tube to radially contract to an inner diameter equal to its original inside diameter of three mm.

Example 18

One hundred grams of FLUON CD123 resin produced by ICI Americas, Inc. was sifted through a No. 10 sieve and then blended at room temperature with twenty-five grams of ISOPAR M solvent (lubricant level 25%) produced by Exxon Corporation to produce a preform blend.

The resulting preform blend was allowed to sit for over eight hours before being re-sifted through a No. 10 sieve.

A preform charge 10 was created by compacting the preform blend under 200 to 400 psi for approximately one minute in a stainless steel cylinder containing a center shaft. The center shaft extended along the centerline X of the cylinder and was concentric with the cylinder. The resulting preform charge 10 was a hollow cylindrical mass having a doughnut shaped circular cross sectional area 13, as shown in FIG. 1. The cylindrical hollow midsection 15 in the preform charge 10 was occupied by the center shaft. The preform charge 10 was then loaded into a cylindrical barrel in a ram extruder and was extruded into several individual lengths of cylindrical thin-walled tubing 11 at a reduction ratio (RR) of 48:1. The total length of tubing 11 produced from the preform charge 10 was about twenty feet. The extruded tubing 11 had an inner diameter of five mm and had a microstructure characterized by nodes interconnected by fibrils.

The solvent was removed from the extruded tubing by placing the tubes in a forced-air circulation electric oven at 255 degrees C. for thirty minutes. As used herein, the length of the tube after it is extruded and heated at 255 degrees C. to remove the solvent is termed the original length of the tube.

A tube nine centimeters long was selected. After being heated to 255 degrees C., each tube was heated to 290 degrees C. for five minutes and was then stretched longitudinally for the first time at rate of about 100% per second to a length four times the original length of the tube, i.e., to a tube thirty-six cm long.

The stretched porous thirty-six cm long tube was then sintered at approximately 360 degrees C. for forty-five to ninety seconds. The sintering crystallized the PTFE and increased the strength of the porous tubes. During sintering each end of the tube was restrained to prevent longitudinal shrinkage of the tube. The resulting stretched, sintered, porous tubes consisted essentially of highly crystalline PTFE polymer and had a microstructure characterized by nodes interconnected by fibrils.

The sintered thirty-six cm long tube was pre-dilated by radially dilating the tube along its entire length to a twenty-four mm inner diameter. The tube was dilated by using an angioplasty balloon catheter in the manner described in Example 3.

The dilated tube was re-sintered at 355 degrees C. for four minutes to cause the tube to contract radially and return to its original diameter of five mm and original length of nine cm. The tube was not restrained during sintering. Sintering the dilated tube at 355 degrees C. completed the pre-dilation procedure.

The pre-dilated five mm diameter and nine cm long tube was heated to 300 degrees C. for five minutes and stretched a second time to a length of eighteen centimeters.

Example 19

The eighteen centimeter long tube produced in Example 18 was tested using the angioplasty balloon catheter and procedure described in Example 5. The results obtained are shown below in Table XI.

TABLE XI

Measurements for Example 18 Tube

| Measurement | Inflation Pressure (Atm) | Outside Diameter (mm) | % Dilatation |
|---|---|---|---|
| 1 | 0 | 6.01 | — |
| 2 | 1 | 6.01 | 0 |
| 3 | 2 | 6.19 | 3 |
| 4 | 3 | 6.80 | 13 |
| 5 | 4.0 | 6.90 | 15 |
| 6 | 5.0 | 7.01 | 17 |

TABLE XI-continued

Measurements for Example 18 Tube

| Measurement | Inflation Pressure (Atm) | Outside Diameter (mm) | % Dilatation |
|---|---|---|---|
| 7 | 6.0 | 7.68 | 28 |
| 8 | 7.0 | 8.40 | 40 |
| 9 | *7.5 | 23.67 | 294 |

*$P_{max}$ and $P_{burst}$
REC = (7.5 atm × 14.7 psi/atm)/294% = 0.375 psi/%
REL = (7.5 atm × 14.7 psi/atm)/294% = 0.375 psi/%
RER = (0.375)/(0.375) = 1.0

From an endovascular grafting perspective, an RER of 1.0 is an ideal value because the maximum pressure is equal to the burst pressure. This permits the ready dilation of a polytetrafluoroethylene tube without exceeding the maximum pressure. Exceeding the maximum pressure results in the loss of structural integrity.

As would be appreciated by those of skill in the art, the amount by which an extruded tube is lengthened before it is sintered to produce highly crystalline polytetrafluoroethylene polymer can be varied as desired to control the amount of pressure required to dilate a tube. The more a tube is lengthened, the less dense the wall of the tube and the less pressure required to dilate the tube. Similarly, the amount by which the tube is pre-dilated can be varied as desired. In Example 18, the tube was pre-dilated to a diameter equal to about five times the original diameter and was lengthened the second time to a length (equal to twice the original extruded length) which was only one-half of the length (equal to four times the original extruded length) at which the tube was pre-dilated to 24 mm. As a result, the max inflation pressure occurred when the tube was radially dilated to an outer diameter of about 23.67 mm. The amount by which the tube is lengthened the second time and the amount of pre-dilated can be varied to alter the amount of tube dilation required to reach the max inflation pressure, $P_{max}$.

Example 20

Example 18 was repeated, except that after the pre-dilated tube was five mm inner diameter and nine cm long tube was heated to 300 degrees C. for five minutes and stretched a second time, the tube was stretched to a length of thirteen and a half centimeters instead of a length of eighteen centimeters.

Example 21

The thirteen and a half centimeters long tube produced in Example 20 was tested using the angioplasty balloon catheter and procedure described in Example 5. The results obtained are shown below in Table XII.

TABLE XII

Measurements for Example 20 Tube

| Measurement | Inflation Pressure (Atm) | Outside Diameter (mm) | % Dilatation |
|---|---|---|---|
| 1 | 0 | 6.48 | — |
| 2 | 3 | 6.48 | 0 |
| 3 | 4 | 6.71 | 4 |
| 4 | 5 | 6.71 | 4 |
| 5 | 6 | 6.87 | 6 |
| 6 | 7 | 6.87 | 6 |
| 7 | 8 | 6.87 | 6 |
| 8 | 9 | 7.17 | 11 |

TABLE XII-continued

Measurements for Example 20 Tube

| Measurement | Inflation Pressure (Atm) | Outside Diameter (mm) | % Dilatation |
|---|---|---|---|
| 9 | 10 | 7.83 | 21 |
| 10 | 11 | 8.68 | 34 |
| 11 | 12 | 11.92 | 84 |
| 12 | *12.5 | 24.28 | 275 |

*$P_{max}$ and $P_{burst}$
REC = (12.5 atm × 14.7 psi/atm)/275% = 0.69 psi/%
REL = (12.5 atm × 14.7 psi/atm)/275% = 0.69 psi/%
RER = (0.69)/(0.69) = 1.0

The results in Table XII demonstrate how increasing the density of the wall of the tubing also increased the pressure needed to dilate the tubing. The density of the wall of the tube is increased by reducing the amount by which the tube is stretched. The $P_{max}$ and percent dilatation at $P_{max}$ can be adjusted to reasonable desired values by varying the amount by which the tube is pre-dilated and the amount by which the tube is stretched. The values of $P_{max}$ and percent dilatation at $P_{max}$ are limited by the physical properties of the polytetrafluoroethylene utilized to prepare the tubing.

Example 22

One hundred grams of FLUON CD 123 resin produced by ICI Americas, Inc. was sifted through a No. 10 sieve and then blended at room temperature with eighteen grams of ISOPAR M solvent (18% lubricant level) produced by Exxon Corporation to produce a preform blend.

The resulting preform blend was allowed to sit for over eight hours before being re-sifted through a No. 10 sieve. A preform charge 10 was created by compacting the preform blend under 200 to 400 psi for approximately one minute in a stainless steel cylinder containing a center shaft. The center shaft extended along the centerline X of the cylinder and was concentric with the cylinder. The resulting preform charge 10 was a hollow cylindrical mass having a doughnut shaped circular cross sectional area 13, as shown in FIG. 1. The cylindrical hollow midsection 15 in the preform charge 10 was occupied by the center shaft. The preform charge 10 was then loaded into a cylindrical barrel in a ram extruder and extruded into several individual lengths of cylindrical thin-walled tubing 11 at a reduction ratio (RR) of 51:1. The total length of tubing 11 produced from the preform charge 10 was about twenty feet. The extruded tubing 11 had an inner diameter of three mm and had a microstructure characterized by nodes interconnected by fibrils.

The solvent was removed from the extruded tubing by placing the tubes in a forced-air circulation electric oven at 255 degrees C. for thirty minutes. As used herein, the length of the tube after it is extruded and heated at 255 degrees C. to remove the solvent is termed the original length of the tube.

First and second tubes each nine centimeters long were selected. After being heated to 255 degrees C., each tube was heated to 290 degrees C. for five minutes and was then stretched longitudinally for the first time at rate of about 100% per second to a length three times the original length of the tube, i.e., to a tube twenty-seven cm long.

The pair of stretched porous twenty-seven cm long tubes were then sintered at approximately 360 degrees C. for forty-five to ninety seconds. The sintering crystallized the PTFE and increased the strength of the porous tubes. During sintering each end of the tube was restrained to prevent longitudinal shrinkage of the tube. The resulting stretched, sintered, porous tubes consisted essentially of highly crystalline PTFE polymer and had a microstructure characterized by nodes interconnected by fibrils.

The first sintered twenty-seven cm long tube was tested using the angioplasty balloon catheter and procedure described in Example 5. The results obtained are shown below in Table XIII.

TABLE XIII

Measurements for First Example 22 Tube

| Measurement | Inflation Pressure (Atm) | Outside Diameter (mm) | % Dilatation |
|---|---|---|---|
| 1 | 0 | 5.34 | — |
| 2 | 1 | 5.43 | 2 |
| 3 | 2 | 5.43 | 2 |
| 4 | 3 | 5.43 | 2 |
| 5 | 4 | 5.43 | 2 |
| 6 | 5 | 5.58 | 4 |
| 7 | 6 ($P_{max}$) | 6.55 | 23 |
| 8 | 5 ($P_{burst}$) | 20.76 | 291 |

REC = 3.83 psi/%
REL = 0.25 psi/%
RER = 15.3

The second sintered twenty-seven cm long tube was pre-dilated by radially dilating the tube along its entire length to a ten mm inner diameter. The tube was dilated by using an angioplasty balloon catheter in the manner described in Example 3.

The dilated tube was re-sintered at 355 degrees C. for four minutes to cause the tube to radially contract and return to its original diameter of three mm and original length of nine cm. Sintering the dilated tube at 355 degrees C. completed the pre-dilation procedure.

The pre-dilated five mm diameter and nine cm long tube was heated to 300 degrees C. for five minutes and stretched a second time to a length of eighteen centimeters. The eighteen centimeter pre-dilated tube produced in this Example 22 was then tested using the angioplasty balloon catheter and procedure described in Example 5. The results obtained are shown below in Table XIV.

TABLE XIV

Measurements for Second Example 22 Tube (Pre-Dilated)

| Measurement | Inflation Pressure (Atm) | Outside Diameter (mm) | % Dilatation |
|---|---|---|---|
| 1 | 0 | 5.38 | — |
| 2 | 1 | 5.38 | 0 |
| 3 | 2 | 5.38 | 0 |
| 4 | 3 | 5.38 | 0 |
| 5 | 4 | 5.38 | 0 |
| 6 | 5 | 5.38 | 0 |
| 7 | 6 ($P_{max}$) | 6.56 | 22 |
| 8 | 5.5 ($P_{burst}$) | 19.26 | 258 |

REC = 4.01 psi/%
REL = 0.31 psi/%
RER = 12.9

Example 23

One hundred grams of FLUON CD123 resin produced by ICI Americas, Inc. was sifted through a No. 10 sieve and then blended at room temperature with eighteen grams of ISOPAR M solvent (18% lubricant level) produced by Exxon Corporation to produce a preform blend.

The resulting preform blend was allowed to sit for over eight hours before being re-sifted through a No. 10 sieve. A preform charge 10 was created by compacting the preform blend under 200 to 400 psi for approximately one minute in a stainless steel cylinder containing a center shaft. The center shaft extended along the centerline X of the cylinder and was concentric with the cylinder. The resulting preform charge 10 was a hollow cylindrical mass having a doughnut shaped circular cross sectional area 13, as shown in FIG. 1. The cylindrical hollow midsection 15 in the preform charge 10 was occupied by the center shaft. The preform charge 10 was then loaded into a cylindrical barrel in a ram extruder and was extruded into several individual lengths of cylindrical thin-walled tubing 11 at a reduction ratio (RR) of 51:1. The total length of tubing 11 produced from the preform charge 10 was about twenty feet. The extruded tubing 11 had an inner diameter of three mm and had a microstructure characterized by nodes interconnected by fibrils.

The solvent was removed from the extruded tubing by placing the tubes in a forced-air circulation electric oven at 255 degrees C. for thirty minutes. As used herein, the length of the tube after it is extruded and heated at 255 degrees C. to remove the solvent is termed the original length of the tube.

First, second, and third tubes each nine centimeters long were selected. After being heated to 255 degrees C., each tube was heated to 290 degrees C. for five minutes and was then stretched longitudinally for the first time at a rate of about 100% per second to a length seven times the original length of the tube, i.e., to a tube sixty-three cm long.

The trio of stretched porous sixty-three cm long tubes were then sintered at approximately 360 degrees C. for forty-five to ninety seconds. The sintering crystallized the PTFE and increased the strength of the porous tubes. During sintering each end of the tube was restrained to prevent longitudinal shrinkage of the tube. The resulting stretched, sintered, porous tubes consisted essentially of highly crystalline PTFE polymer and had a microstructure characterized by nodes interconnected by fibrils.

The first sintered sixty-three cm long tube was tested using the angioplasty balloon catheter and procedure described in Example 5. The angioplasty balloon was about four cm long. The results obtained are shown below in Table XV.

TABLE XV

Measurements for First Example 23 Tube (Tube Not Pre-Dilated)

| Measurement | Inflation Pressure (Atm) | Outside Diameter (mm) | % Dilatation |
|---|---|---|---|
| 1 | 0 | 5.66 | — |
| 2 | 1 | 5.66 | 0 |
| 3 | 2 | 5.66 | 0 |
| 4 | 3 ($P_{max}$) | 5.76 | 19 |
| 5 | 2.8 ($P_{burst}$) | 19.92 | 252 |

REC = 2.32 psi/%
REL = 0.16 psi/%
RER = 14.5

The second sintered sixty-three cm long tube was pre-dilated by radially dilating the tube along its entire length to a ten mm inner diameter. The tube was dilated by using an angioplasty balloon catheter in the manner described in Example 3.

The dilated second tube was restrained longitudinally (so the tube could not contract to a shorter length) and was re-sintered at 350 degrees C. for thirty seconds to cause the second tube to return to its original diameter of three mm. After sintering at 350 degrees C., the length of the second tube was the same, i.e., sixty-three cm. Sintering the dilated second tube at 350 degrees C. for thirty seconds completed the pre-dilation procedure for the second tube.

The pre-dilated three mm diameter and sixty-three cm long second tube was tested using the angioplasty balloon catheter and procedure described in Example 5. The angioplasty balloon was four cm long. The results obtained are shown below in Table XVI.

TABLE XVI

Measurements for Second Example 23 Tube (Pre-Dilated; Sintered Under Longitudinal Restraint)

| Measurement | Inflation Pressure (Atm) | Outside Diameter (mm) | % Dilatation |
|---|---|---|---|
| 1 | 0 | 5.37 | — |
| 2 | 1 | 5.72 | 7 |
| 3 | 2 | 5.82 | 8 |
| 4 | 3 ($P_{max}$) | 7.78 | 45 |
| 5 | 2.8 ($P_{burst}$) | 20.78 | 287 |

REC = 0.98 psi/%
REL = 0.14 psi/%
RER = 7.0

The third sintered sixty-three cm long tube was pre-dilated by radially dilating the tube along its entire length to a fifteen mm inner diameter. The tube was dilated by using an angioplasty balloon catheter in the manner described in Example 3.

The dilated third tube was restrained longitudinally (so the tube could not contract to a shorter length) and was re-sintered at 350 degrees C. for thirty seconds to cause the tube to return to its original diameter of three mm. The length of the third tube remained the same, i.e., sixty-three cm. Sintering the dilated third tube at 350 degrees C. for thirty seconds completed the pre-dilation procedure for the third tube.

The pre-dilated three mm diameter and sixty-three cm long third tube was tested using the angioplasty balloon catheter and procedure described in Example 5. The angioplasty balloon was four cm long. The results obtained are shown below in Table XVII.

TABLE XVII

Measurements for Third Example 23 Tube (Pre-Dilated; Sintered Under Longitudinal Restraint)

| Measurement | Inflation Pressure (Atm) | Outside Diameter (mm) | % Dilatation |
|---|---|---|---|
| 1 | 0 | 6.00 | — |
| 2 | 1 | 6.00 | 0 |
| 3 | 2 | 7.68 | 28 |
| 4 | *2.5 | 21.14 | 252 |

*$P_{max}$ and $P_{burst}$
REC = 0.15 psi/%
REL = 0.15 psi/%
RER = 1.0

As evidenced in this Example 23, the PTFE tubing had to be significantly pre-dilated, i.e. up to a diameter equal to five times the original diameter, in order to obtain an RER of 1. The amount of pre-dilation necessary to obtain an RER of 1 can be determined for each particular lubricant—PTFE resin composition and for each selected longitudinal expansion (stretching) of an extruded tube which is used prior to sintering of an extruded tube to produce a high crystalline PTFE structure. A tube having an RER of 1 will not rupture because when the tube is expanded to a diameter less than the diameter to which the tube is expanded during pre-dilation, the tube retains its structural integrity.

As would be appreciated by those of skill in the art, after a PTFE tube (or sheet or other shaped PTFE article) is (a) lengthened to a first length by being stretched along its longitudinal axis prior to being initially sintered to form a highly crystalline PTFE polymer, and (b) pre-dilated, the tube can again be lengthened by being stretched a second time along it longitudinal axis to a second length less than, equal to, or greater than said first length.

The present invention has been described above in terms of certain preferred embodiments so that an understanding of the present invention can be conveyed. However, there are many alternative arrangements not specifically described herein, but with which the present invention is applicable. The scope of the present invention should therefore not be limited by the embodiments illustrated, but rather it should be understood that the present invention has wide applicability with respect to expanded PTFE generally. All modifications, variations, or equivalent elements and implementations that are within the scope of the appended claims should therefore be considered within the scope of the invention.

The invention claimed is:

1. A method of making a liner for an expandable stent, comprising:
   extruding a polytetrafluoroethylene tube having a first length;
   stretching the extruded tube to a second length greater than the first length;
   sintering the stretched tube while restrained from longitudinal contraction;
   dilating the sintered stretched tube from a first diameter to a second diameter larger than the first diameter; and
   sintering the dilated tube while unrestrained to permit radial and longitudinal contraction, the contracted tube having a radial expansion ratio of about 1.0.

2. The method according to claim 1, wherein the stretching step includes stretching the extruded tube to a second length approximately four times greater than the first length.

3. The method according to claim 2, wherein the dilating step includes dilating the sintered stretched tube to a second diameter approximately five times greater than the first diameter.

4. The method according to claim 1, further comprising longitudinally stretching the tube following the second sintering step to a length greater than the first length.

5. The method according to claim 4, wherein the longitudinally stretching step following the second sintering step includes stretching the tube to a length approximately two times greater than the first length.

6. The method according to claim 4, wherein the longitudinally stretching step following the second sintering step includes stretching the tube to a length less than two times the first length.

7. The method according to claim 1, wherein the dilating step further comprises restraining the tube from longitudinal contraction.

8. The method according to claim 7, wherein the dilating step includes dilating the sintered stretched tube to a second diameter approximately five times greater than the first diameter.

9. A method of making an endoluminal device, comprising:
   providing an expandable stent;
   forming a liner, comprising:
      extruding a polytetrafluoroethylene tube having a first length;
      stretching the extruded tube to a second length greater than the first length;
      sintering the stretched tube while restrained from longitudinal contraction;
      dilating the sintered stretched tube from a first diameter to a second diameter larger than the first diameter;
      sintering the dilated tube while unrestrained to permit radial and longitudinal contraction, the contracted tube having a radial expansion ratio of about 1.0; and
      stretching the tube following the second sintering step to a length greater than the first length; and
   associating the liner with the stent.

10. The method according to claim 9, wherein the first stretching step includes stretching the extruded tube to a second length approximately four times greater than the first length.

11. The method according to claim 10, wherein the dilating step includes dilating the sintered stretched tube to a second diameter approximately five times greater than the first diameter.

12. The method according to claim 9, wherein the second stretching step includes stretching the tube to a length approximately two times greater than the first length.

13. The method according to claim 9, wherein the second stretching step includes stretching the tube to a length less than two times the first length.

14. The method according to claim 9, wherein the dilating step further comprises restraining the tube from longitudinal contraction.

15. The method according to claim 14, wherein the dilating step includes dilating the sintered stretched tube to a second diameter approximately five times greater than the first diameter.

16. A method of making a polytetrafluoroethylene product, comprising:
   extruding a polytetrafluoroethylene tube having a first length;
   stretching the extruded tube to a second length greater than the first length;
   sintering the stretched tube while restrained from longitudinal contraction;
   dilating the sintered stretched tube from a first diameter to a second diameter larger than the first diameter;
   sintering the dilated tube while unrestrained to substantially contract the tube to the first length and the first diameter, the contracted tube having a radial expansion ratio of about 1.0; and
   stretching the contracted tube to a third length greater than the first length.

17. The method according to claim 16, wherein the third length is approximately two times greater than the first length.

18. The method according to claim 16, wherein the third length is less than two times the first length.

19. The method according to claim 16, wherein the second length is approximately four times greater than the first length.

20. The method according to claim 16, wherein the second diameter is approximately five times greater than the first diameter.

* * * * *